United States Patent [19]
Steinert

[11] Patent Number: 5,451,230
[45] Date of Patent: Sep. 19, 1995

[54] CATARACT DISASSEMBLY

[76] Inventor: Roger F. Steinert, 83 Sandra La., North Andover, Mass. 01845

[21] Appl. No.: 320,459

[22] Filed: Oct. 11, 1994

[51] Int. Cl.$^6$ .............................................. A61B 17/00
[52] U.S. Cl. ........................................ 606/107; 606/1; 606/161
[58] Field of Search .................. 606/1, 106, 107, 161, 606/162, 160, 190

[56] References Cited

U.S. PATENT DOCUMENTS

| | | | |
|---|---|---|---|
| 4,530,117 | 7/1985 | Kelman | 606/107 X |
| 4,579,116 | 4/1986 | Catalano | 606/107 |
| 5,154,694 | 10/1992 | Kelman | 606/107 X |
| 5,174,279 | 12/1992 | Cobo et al. | 606/107 |
| 5,188,125 | 2/1993 | Kilmer et al. | 606/107 |
| 5,282,796 | 2/1994 | Knoepfler | 606/1 |
| 5,352,219 | 10/1994 | Reddy | 606/1 |

OTHER PUBLICATIONS

Koch et al., J. Cataract Refract Surg. 20:566–570, 1994.
Shepherd, J. Cataract Refract Surg. 16:436–440, 1990.
Fine, J. Cataract Refract Surg. 17:366–371, 1991.
Gimbel, J. Cataract Refract Surg. 17:281–291, 1991.
Fine, J. Cataract Refract Surg. 18:508–512, 1992.
Fine, et al., J. Cataract Refract Surg. 19:797–802, 1993.

*Primary Examiner*—Peter A. Aschenbrenner
*Attorney, Agent, or Firm*—Fish & Richardson

[57] ABSTRACT

An instrument to facilitate nuclear disassembly during cataract surgery includes a proximal handle, a shaft portion axially aligned with the proximal handle, an intermediate portion constructed to traverse the cortex of the eye, and a hook-form distal end. An inner region of the hook-form has a leading edge defined by diverging surfaces. The diverging surfaces lie at an acute splitting angle to one another selected to have a wedging effect when the leading edge is drawn along a cleavage plane of the nucleus. The diverging surfaces define a relatively bulky back portion that imparts desired stiffness to the leading edge. The hook-form is shaped to facilitate maintaining contact with the nucleus while the leading edge is drawn along the cleavage plane. A method of performing nuclear disassembly during cataract surgery utilizing the instrument is also described.

11 Claims, 3 Drawing Sheets

CATARACT DISASSEMBLY

BACKGROUND OF THE INVENTION

This invention relates in general to instruments and methods of removing a cataractous lens. More particularly, it relates to an instrument and method for cataract disassembly.

Clouding of the natural crystalline lens of the eye is termed "cataract formation". To restore vision, the cataractous lens must be removed. It has been known to perform cataract surgery using a technique which "disassembles" the hard central nucleus of the lens into a number of fragments to be removed progressively from the eye. The nucleus is disassembled using a bent wire hook made out of round stiff surgical wire material and the resulting pieces of the lens nucleus are aspirated. Typically the lens is stabilized by a phacoemulsifier while the hook is drawn across the nucleus. The hook has typically been of approximate "L" shape, with a portion extending at substantially a right angle to the shaft of the instrument.

In order to disassemble the appropriate size nuclear fragments without encountering difficulties in containing the nuclear fragments within the posterior capsular sac away from the corneal endothelium, it has been known to create a central trough or crater in the nucleus using the phacoemulsifier alone or in combination with the hook, followed by splitting the nucleus into two halves with the hook. These two large nuclear pieces, due to their bulk, remain stable within the posterior capsular sac. The hook is drawn across the nuclear pieces following the natural cleavage planes progressively splitting off only small wedges in a circumferential direction. Although the technique as described has had a modicum of success, difficulties have been encountered in that the hook has tended to slip and lose contact with the nucleus during the drawing motion.

SUMMARY OF THE INVENTION

It is realized, according to the invention, that highly controlled, safe and predictable disassembly of the nucleus can be performed by providing an instrument having a curved, wedge-shaped distal end which facilitates maintaining contact with the nucleus.

An important aspect of the invention relates to an instrument to facilitate nuclear disassembly during cataract surgery, for use with a nucleus stabilizer, including a proximal handle, a shaft portion axially aligned with the proximal handle, an intermediate portion extending at an angle to the handle and constructed to traverse the cortex of the eye, and a curved, hook-form distal end portion. The curved, hook-form distal end portion has a leading edge on an inner region of the hook-form defined by diverging surfaces. The diverging surfaces lie at an acute splitting angle to one another selected to have a wedging effect when the leading edge is drawn along a cleavage plane of the nucleus. The diverging surfaces extend sufficiently to define a relatively bulky back portion that imparts desired stiffness to the leading edge to enable the leading edge to strongly contact the nucleus. The curved hook-form distal end portion is shaped to facilitate maintaining contact with the nucleus while the leading edge is drawn along the cleavage plane.

Preferred embodiments of this aspect of the invention include one or more of the following features.

The acute splitting angle is about 35° and curved distal end is in the range of 1.25–2.5 mm in length, preferably 1.5 mm. The leading edge is in the range of 1.25–2 mm in length, preferably 1.25 mm. The intermediate portion is gently curved.

Another aspect of the invention concerns a method of performing nuclear disassembly during cataract surgery, including the steps of inserting a nuclear stabilizer into the eye, inserting a second instrument into the eye into contact with the nucleus, the instrument having a proximal handle, a shaft portion axially aligned with the proximal handle, an intermediate portion extending at an angle to the handle and constructed to traverse the cortex, and a curved, hook-form distal end portion having a leading edge on an inner region of the hook-form defined by diverging surfaces. The diverging surfaces lie at an acute splitting angle to one another. The angle is selected to have a wedging effect when the leading edge is drawn along a cleavage plane of the nucleus. The diverging surfaces extending sufficiently to define a relatively bulky back portion that imparts desired stiffness to the leading edge, to enable the leading edge to strongly contact the nucleus. The curved hook-form distal end portion is shaped to facilitate maintaining contact with the nucleus while the leading edge is drawn along the cleavage plane. The wedge-shaped portion is drawn across the nucleus while the nucleus is stabilized by the nuclear stabilizer to split the nucleus into nuclear fragments taking advantage of the natural cleavage planes in the nucleus by entering the leading edge into the nucleus along a cleavage plane and wedging the nucleus apart while drawing the leading edge along the cleavage plane. Repeatedly positioning nuclear fragments to be stabilized against the nucleus stabilizer by maneuvering a nuclear fragment with the curved distal end, stabilizing the nuclear fragment with the nuclear stabilizer, drawing the wedge-shaped portion across the nuclear fragment while the nuclear fragment is stabilized against the nuclear stabilizer to split a desired size piece off the nuclear fragment while taking advantage of the natural cleavage planes in the nuclear fragment by entering the leading edge into the nuclear fragment along a cleavage plane and wedging the nuclear fragment apart while drawing the leading edge along the cleavage plane to create the desired sized piece. The desired sized piece is sized to fit through an aspiration tube, and the desired sized piece is aspirated from the eye.

Preferred embodiments of this aspect of the invention include one or more of the following features.

The nuclear stabilizer is a phacoemulsifier and the nuclear fragment is stabilized by burying a tip of the phacoemulsifier into the nuclear fragment and the desired sized piece is aspirated through a tube of the phacoemulsifier. The phacoemulsifier is used under high vacuum. A center area of the nucleus is debulked with ultrasound energy from the phacoemulsifier prior to splitting the nucleus.

DESCRIPTION OF THE PREFERRED EMBODIMENT

Figure 1:
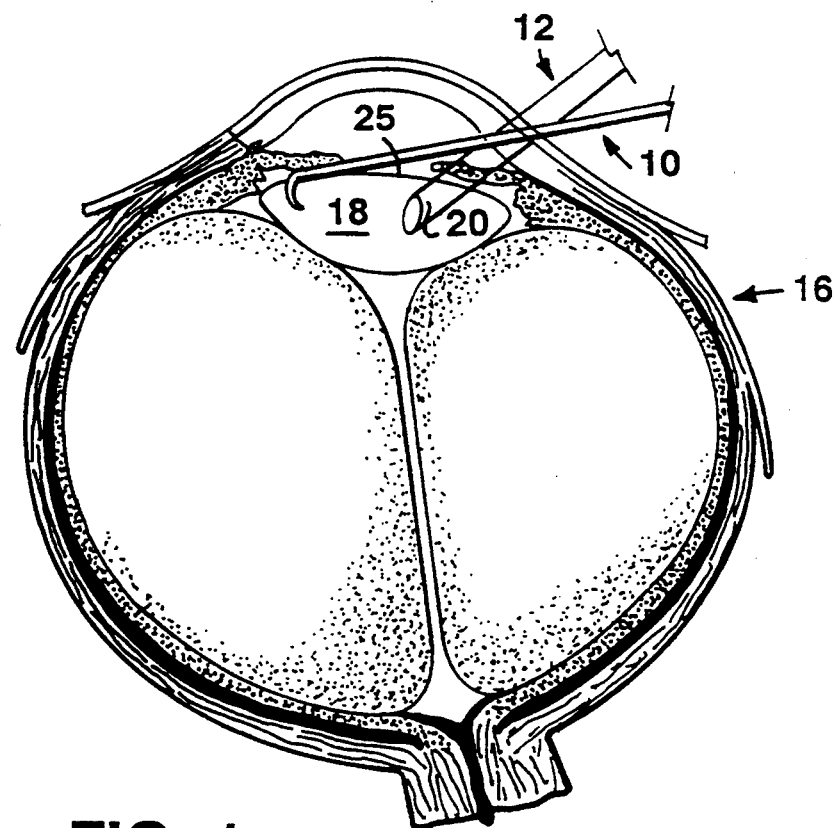
FIG. 1 is a diagrammatic illustration of the instrument of the present invention inserted into the cataractous lens of an eye.

As shown in FIG. 1, the firm nucleus of a cataract lens can be disassembled during cataract surgery utilizing instrument 10 in conjunction with a nuclear stabilizer, e.g., phacoemulsifier 12. Instrument 10 is inserted into eye 16 across the hard nucleus 18 of a cataractous lens. With nucleus 18 held in place by the tip 20 of phacoemulsifier 12, instrument 10 engages nucleus 18. Instrument 10 is then drawn laterally across nucleus 18, resulting in the controlled formation of fragments of nucleus 18, to facilitate safe and controlled removal of the cataractous lens.

Figure 2:
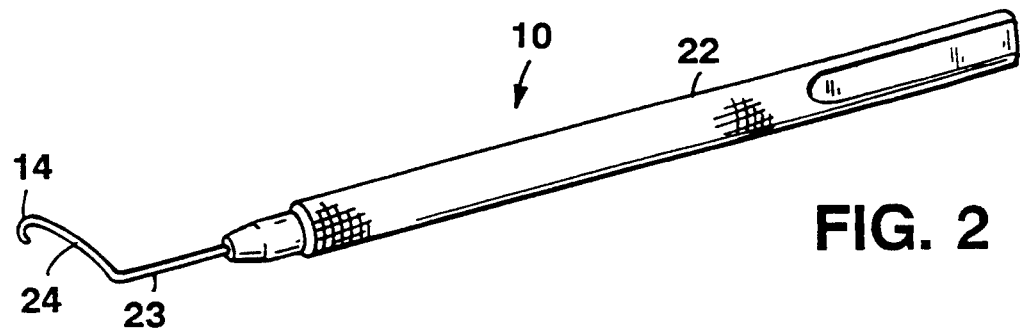
FIG. 2 is a perspective view of the instrument.

Referring to FIG. 2, instrument 10 includes a proximal handle 22, a first shaft portion 23 axially aligned with the handle, a gently curved intermediate portion 24 constructed to traverse the anterior lens 25 of eye 16 and a relatively tightly curved distal end 14. First shaft portion 23 has a length, e.g., of 1.4 cm. Tightly curved distal end 14 has a length in the range of 1.25 to 2.5 mm, preferably 1.5 mm, measured along the curve, and an arc radius of about 1 mm.

Figure 2A:
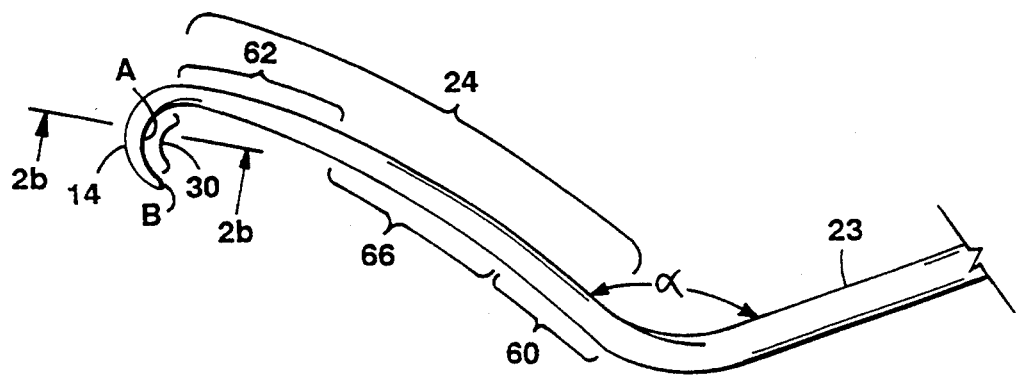
FIG. 2a is an enlargement of the distal section of FIG. 2.

Referring also to FIG. 2a, an initial relatively straight component 60 of intermediate portion 24 having a length, e.g., of 2.5 mm, extends at an angle α of about 75° to the axis of shaft 23. A curved portion 66 having a length of 3.0 mm measured along the curve and an arc radius of about 1.0 cm extends from initial component 60 to a relatively straight tapered outward component 62 of intermediate portion 24 having a length, e.g., of 0.3 cm. Tapered outward component 62 is wider in the region of curved portion 66, e.g., 0.4 mm in diameter, and narrower in the region of tightly curved distal end 14, e.g., 0.3 mm in diameter.

Figure 2B:
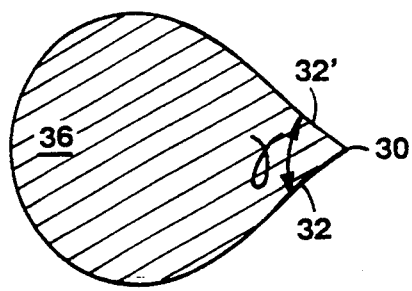
FIG. 2b is a cross-section of the distal portion of the instrument taken along lines 2b–2b.
Figure 2C:
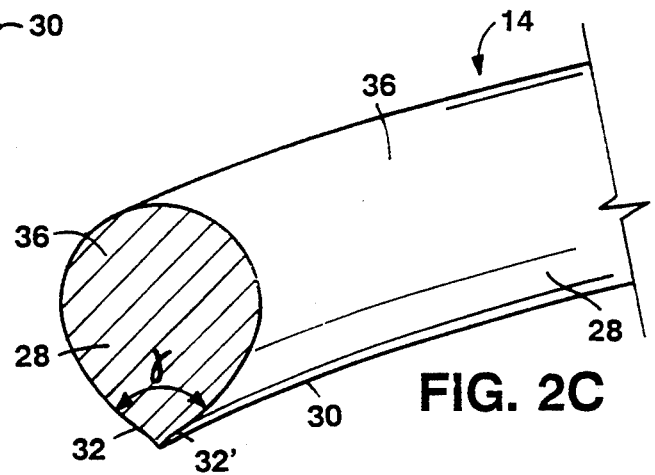
FIG. 2c is an enlarged perspective view of the distal portion of the instrument shown in FIG. 2b.
Figure 4:
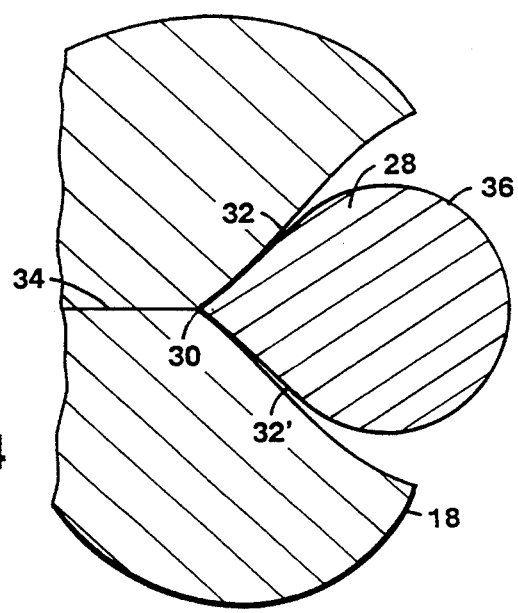
FIG. 4 shows the wedging action of the instrument.

Referring also to FIGS. 2b and 2c, a sharpened leading edge section 30 of an inner region 15 of tightly curved distal end 14 having a length, e.g., in the range of about 1.25 to 2.0 mm, preferably 1.5 mm, is defined by a wedge-shaped portion 28 having intersecting diverging surfaces 32, 32'. The surfaces form an acute splitting angle γ, preferably 35° selected to have a wedging effect when edge 30 is drawn along a cleavage plane 34 (FIG. 4) of nucleus 18.

Figure 3:
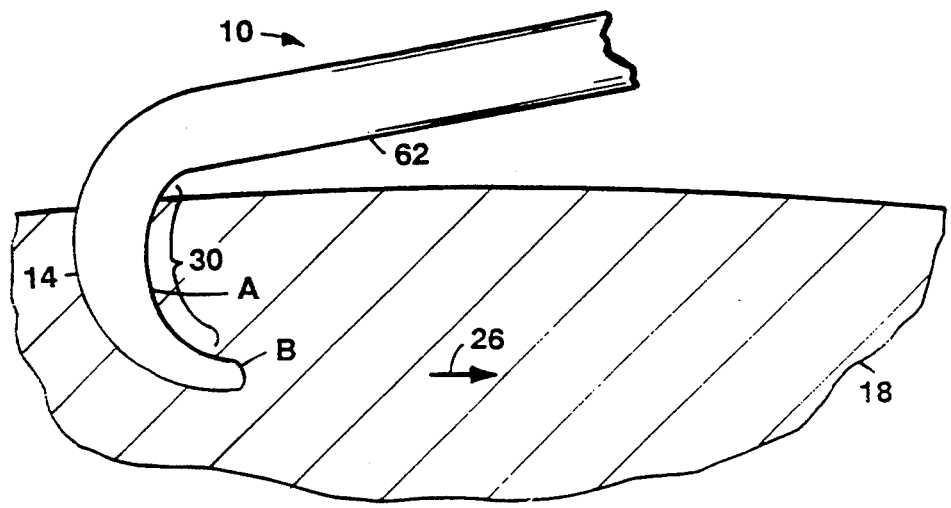
FIG. 3 is an enlarged side view of the distal portion of the instrument shown positioned within the cataractous lens of an eye.

Tightly curved distal end 14 is shaped to facilitate maintaining contact with nucleus 18 while edge 30 is drawn along cleavage plane 34. Referring to FIGS. 2a and 3, curved distal end 14 is configured with the leading tip, point B, ahead of the mid, cutting region, point A, so that while edge 30 is drawn in the direction of arrow 26, the form of instrument 10 maintains edge 30 in contact with nucleus 18. The diverging surfaces extend to a widened back region 36, FIGS. 2b and 2c, that has relatively substantial bulk that imparts desired stiffness to edge 30 to enable edge 30 to strongly contact nucleus 18. This stiffness enables tightly curved distal end 14, i.e., the principal hook formation, to have a length as short as 1.25 mm, while ensuring strong contact with nucleus 18, and provides a margin of safety between the tip of instrument 10 and the posterior capsule of the eye, even in the peripheral region.

Figure 5:
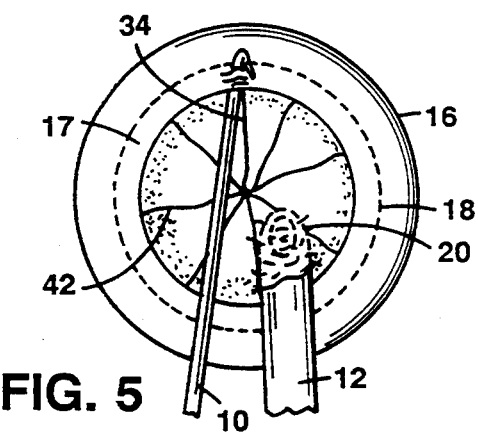
FIGS. 5–5c show the instrument in operation removing a cataractous lens of an eye.
Figure 5A:
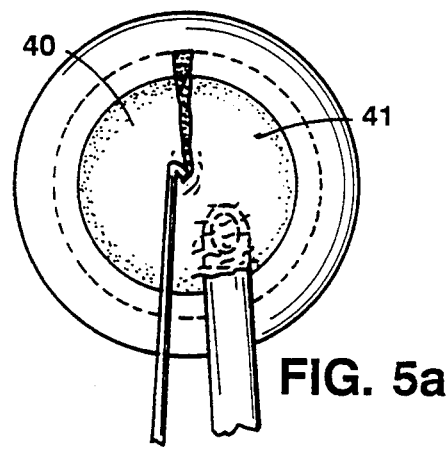
Figure 5B:
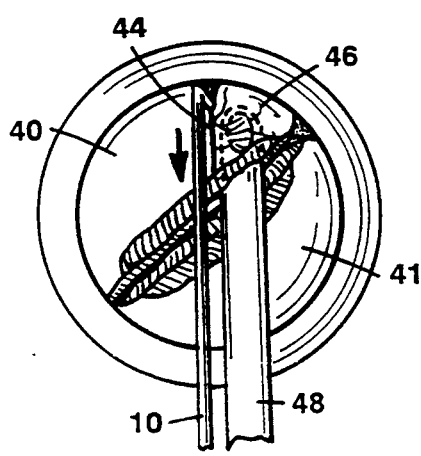
Figure 5C:
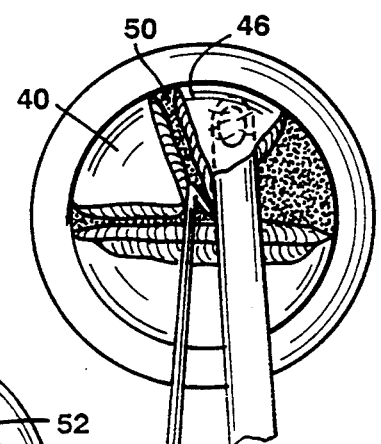

Referring to FIGS. 5–5c, in operation, nucleus 18 is stabilized with phacoemulsification tip 20 by burying tip 20 just short of the center of nucleus 18 using ultrasound energy. Instrument 10 is then inserted into eye 16 into contact with nucleus 18, with the tightly curved hook portion engaged on an edge of the nucleus. Edge 30 of tightly curved distal end 14 is drawn across nucleus 18 from the equatorial side of the outer nucleus toward the center and in the anteroposterior direction creating lateral forces which split nucleus 18 into nuclear fragments 40, 41.

It is important for tightly curved distal end 14 to be under the edge of the anterior capsulorhexis 17. Prior successful hydrodelineation is helpful in recognizing this boundary, although instrument 10 will tend to naturally find this plane.

Generally the nucleus will fracture once the center of the nucleus is passed by wedge-shaped portion 28. The splitting action takes advantage of the natural cleavage planes 42 in the nucleus by entering edge 30 into nucleus 18 along a cleavage plane 34 and wedging nucleus 18 apart while drawing edge 30 along cleavage plane 34.

Referring to FIG. 5b, instrument 10 is then repositioned and the wedge-shaped portion 28 drawn across nuclear fragment 40 along cleavage plane 44 to split a desired sized piece 46, sized to fit through an aspiration tube 48 of phacoemulsifier 12 with minimal additional ultrasound energy, off the larger nuclear fragment 40. Desired size piece 46 is then aspirated through aspiration tube 48.

The remainder of nuclear fragment 40 is positioned against phacoemulsification tip 20 by maneuvering nuclear fragment 40 with curved distal end 14. Phacoemulsification tip 20 is then buried into nuclear fragment 40 while nuclear fragment 40 is stabilized against phacoemulsification tip 20 with curved distal end 14.

Referring to FIG. 5c, edge 30 is drawn across nuclear fragment 40 along cleavage plane 50 to split desired sized piece 46 off nuclear fragment 40. Desired size piece 46 is then aspirated through aspiration tube 48. The procedure is repeated until all of nucleus 18 has been removed.

For a right handed surgeon, it is convenient to proceed with fragment 40 located to the left side, and rotate nucleus 18 in a clockwise direction to continue to perform the maneuver with intermediate portion 24 of instrument 10 and phacoemulsifier 12 lying in the region from 5 to 6 o'clock inferiorly as shown in FIGS. 5b and 5c. For a left handed surgeon, it is convenient to proceed with fragment 41 located to the right side, and rotate nucleus 18 in a counterclockwise direction to continue to perform the maneuver with the instruments in the region from 6 to 7 o'clock inferiorly.

Figure 6:
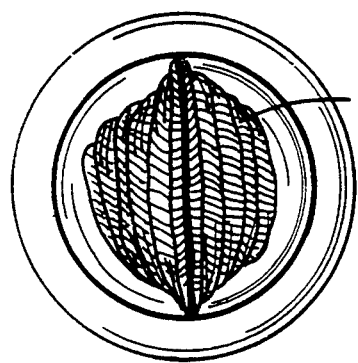
FIG. 6 shows a nucleus with a center region that has been debulked.

This basic splitting procedure works well in lenses of moderate density. In extremely hard nuclei there is a tendency for the splitting procedure to appear to be successful, but the fracture line posteriorly sometimes changes direction and leaves a posterior nuclear plate. This problem can be avoided by performing a conventional cracking maneuver first. Referring to FIG. 6, in this procedure, a center area 52 of nucleus 18 is debulked using ultrasound energy from phacoemulsifier 12, either before or after the original splitting procedure. It is important to leave enough firm peripheral nucleus to be stabilized with phacoemulsifier tip 20 during the subsequent splitting procedures.

Desired sized pieces 46 can be created in virtually any size. If a piece is split and then appears to be too large, it can be split again. The goal is to create pieces sized to fit through aspiration tube 48. The number of desired sized pieces 46 created during the operation may range from about six to sixteen. The number depends upon the density of the nucleus, i.e. the harder the nucleus, the smaller the fragments should be and therefore the larger the number of pieces.

Utilizing a high phacoemulsifier vacuum, e.g., 200 to 700 mm Hg, improves nuclear control and reduces the total ultrasound energy required. The reduction in ultrasound energy is seen as a result of the combination of the manual energy input during the splitting procedure with the energy input from the high vacuum allowing larger nuclear fragments to be aspirated. Because manual energy and vacuum energy are highly localized, there is less collateral damage than experienced with ultrasound, resulting in a safer and more controlled technique.

Other embodiments will occur to those skilled in the art and are within the following claims.

What is claimed is:

1. An instrument to facilitate nuclear disassembly during cataract surgery, for use with a nucleus stabilizer, comprising:
   a proximal handle,
   a shaft portion axially aligned with said proximal handle,
   an intermediate portion extending at an angle to said handle and constructed to traverse the cortex, and
   a curved, hook-form distal end portion having a leading edge on an inner region of said hook-form defined by diverging surfaces, said diverging surfaces lying at an acute splitting angle to one another, said angle selected to have a wedging effect when said leading edge is drawn along a cleavage plane of the nucleus,
   said diverging surfaces extending sufficiently to define a relatively bulky back portion that imparts desired stiffness to said leading edge, to enable said leading edge to strongly contact the nucleus,
   said curved hook-form distal end portion being shaped to facilitate maintaining contact with the nucleus while said leading edge is drawn along the cleavage plane.

2. The instrument of claim 1 wherein said acute splitting angle is about 35°.

3. The instrument of claim 1 wherein the length of said curved distal end is in the range of 1.25–2.5 mm.

4. The instrument of claim 3 wherein the length of said curved distal end is 1.5 mm.

5. The instrument of claim 1 wherein the length of said leading edge is in the range of 1.25–2 mm.

6. The instrument of claim 5 wherein the length of said leading edge is 1.25 mm.

7. The instrument of claim 1 wherein said intermediate portion is gently curved.

8. A method of performing nuclear disassembly during cataract surgery, comprising the steps of:
   inserting a nuclear stabilizer into the eye,
   inserting a second instrument into the eye into contact with the nucleus, said instrument having a proximal handle, a shaft portion axially aligned with said proximal handle, an intermediate portion extending at an angle to said handle and constructed to traverse the cortex, and a curved, hook-form distal end portion having a leading edge on an inner region of said hook-form defined by diverging surfaces, said diverging surfaces lying at an acute splitting angle to one another, said angle selected to have a wedging effect when said leading edge is drawn along a cleavage plane of the nucleus, said diverging surfaces extending sufficiently to define a relatively bulky back portion that imparts desired stiffness to said leading edge, to enable said leading edge to strongly contact the nucleus, said curved hook-form distal end portion being shaped to facilitate maintaining contact with the nucleus while said leading edge is drawn along the cleavage plane,
   drawing said wedge-shaped portion across the nucleus while the nucleus is stabilized by said nuclear stabilizer to split the nucleus into nuclear fragments taking advantage of the natural cleavage planes in the nucleus by entering said leading edge into the nucleus along a cleavage plane and wedging the nucleus apart while drawing said leading edge along the cleavage plane,
   repeatedly positioning nuclear fragments to be stabilized against said nucleus stabilizer by maneuvering a nuclear fragment with said curved distal end,
   stabilizing the nuclear fragment with the nuclear stabilizer,
   drawing said wedge-shaped portion across the nuclear fragment while the nuclear fragment is stabilized against the nuclear stabilizer to split a desired size piece off the nuclear fragment while taking advantage of the natural cleavage planes in the nuclear fragment by entering said leading edge into the nuclear fragment along a cleavage plane and wedging the nuclear fragment apart while drawing said leading edge along the cleavage plane to create the desired sized piece, said desired sized piece being sized to fit through an aspiration tube, and
   aspirating the desired sized piece from the eye.

9. The method of claim 8 wherein the nuclear stabilizer is a phacoemulsifier and the nuclear fragment is stabilized by burying a tip of the phacoemulsifier into the nuclear fragment and the desired sized piece is aspirated through a tube of the phacoemulsifier.

10. The method of claim 9 wherein the phacoemulsifier is used under high vacuum.

11. The method of claim 9 further comprising debulking a center area of the nucleus with ultrasound energy from the phacoemulsifier prior to splitting the nucleus.

* * * * *